US010352839B2

(12) United States Patent
Kanno et al.

(10) Patent No.: US 10,352,839 B2
(45) Date of Patent: Jul. 16, 2019

(54) METHOD AND DEVICE FOR MEASURING PHYSICAL PROPERTIES OF FLUID

(71) Applicant: A&D COMPANY, LIMITED, Tokyo (JP)

(72) Inventors: Masahiro Kanno, Saitama (JP); Yoshikazu Nagane, Saitama (JP)

(73) Assignee: A&D COMPANY, LIMITED, Tokyo (JP)

( * ) Notice: Subject to any disclaimer, the term of this patent is extended or adjusted under 35 U.S.C. 154(b) by 124 days.

(21) Appl. No.: 15/308,766

(22) PCT Filed: Jun. 16, 2014

(86) PCT No.: PCT/JP2014/065890
§ 371 (c)(1),
(2) Date: Nov. 3, 2016

(87) PCT Pub. No.: WO2015/193943
PCT Pub. Date: Dec. 23, 2015

(65) Prior Publication Data
US 2017/0160176 A1 Jun. 8, 2017

(51) Int. Cl.
*G01N 11/16* (2006.01)
*G05B 13/02* (2006.01)

(52) U.S. Cl.
CPC .......... *G01N 11/16* (2013.01); *G01N 11/162* (2013.01); *G05B 13/02* (2013.01); *G05B 13/0205* (2013.01)

(58) Field of Classification Search
CPC ...... G01N 11/16; G01N 11/162; G05B 13/02; G05B 13/0205

USPC ........................................................ 73/54.41
See application file for complete search history.

(56) References Cited

U.S. PATENT DOCUMENTS 3,769,088 A * 10/1973 Seiger ................... H01M 10/42
429/222

FOREIGN PATENT DOCUMENTS

| JP | 56-35206 A | 4/1981 |
|---|---|---|
| JP | 7-160304 A | 6/1995 |
| JP | 7-218415 A | 8/1995 |
| JP | 2009-271251 A | 11/2009 |
| WO | 2011/086879 A1 | 7/2011 |

(Continued)

OTHER PUBLICATIONS

International Search Report dated Sep. 16, 2014 in the corresponding application PCT/JP2014/065890.

*Primary Examiner* — Tarun Sinha
(74) *Attorney, Agent, or Firm* — Roberts Mlotkowski Safran Cole & Calderon P.C.

(57) ABSTRACT

Provided are a method and device for improving a response speed in a measurement of viscosity of a fluid and obtaining a continuous smooth measurement graph. A viscometer includes a machine part that generates a shear rate in a sample, a machine drive, a shear rate changing means that outputs a target shear rate of the machine part, and a displacement detection sensor that measures displacement of the machine part, and performs feedback control to control a driving force of the machine drive so that an output value of the displacement detection sensor corresponds to the target shear rate and measures a viscosity of a sample, wherein a feedback gain is simply set for each measurement according to an optimum design or target shear rate.

2 Claims, 19 Drawing Sheets

(56) References Cited

FOREIGN PATENT DOCUMENTS

| WO | 2014/049698 A1 | 4/2014 | |
| WO | WO-2014049698 A1 * | 4/2014 | ............. G01N 11/16 |

* cited by examiner

METHOD AND DEVICE FOR MEASURING PHYSICAL PROPERTIES OF FLUID

CROSS-REFERENCE TO RELATED APPLICATIONS

The present application is a U.S. National Phase of PCT/JP2014/065890 filed on Jun. 16, 2014. The disclosure of the PCT Application is hereby incorporated by reference into the present Application.

TECHNICAL FIELD

The present invention relates to a method and device for measuring a property of a fluid, particularly, to a method and device for improving a response speed in viscosity measurement and obtaining a continuous measurement graph.

BACKGROUND ART

As a device for measuring a property of a fluid, rotational or vibration viscometers or other type of viscometers are conventionally used. Among these, vibration viscometers include a tuning fork vibration viscometer changeable in shear rate (amplitude of a vibrator) (for example, refer to Patent Literature 1).

FIG. 1 is a configuration diagram of a drive mechanical part 2 of a tuning fork vibration viscometer 1, and FIG. 2 is a block diagram of a control system of the tuning fork vibration viscometer of Patent Literature 1. As shown in FIG. 1, the drive mechanical part 2 includes a pair of vibrators 3 and 3 to be dunked in a sample 4, a magnet 10a and an electromagnetic coil 10b for vibrating the vibrators 3 and 3, and a displacement detection sensor 11 for detecting an amplitude of the vibrators 3 and 3. The tuning fork vibration viscometer of Patent Literature 1 includes, as shown in the block diagram of FIG. 2, a sine wave generating circuit 13, a comparator 14, a controller 15, an I/V converter 16, an A/D converter 17, and a microcontroller 18. A PWM modulation circuit 12 for changing a shear rate (amplitude value) is connected to (or incorporated in) the microcontroller 18.

The tuning fork vibration viscometer controls the pair of vibrators 3 and 3 as control objects, and a driving current to be applied to the electromagnetic coil 10b is feedback-controlled (PID control) by the controller 15 so that an amplitude of the vibrators 3 and 3 corresponds to a target amplitude value (target value) that is modulated in pulse width and input from the microcontroller 18. By utilizing a proportional relationship between a driving current to be applied to the electromagnetic coil 10b and a viscosity of the sample 4, the viscosity of the sample 4 in a case where the amplitude changes is measured.

CITATION LIST

Patent Literature

Patent Literature 1: WO 2014/049698

SUMMARY OF THE INVENTION

Problem to be Solved by the Invention

FIG. 3 is a diagram showing a response speed of the tuning fork vibration viscometer of Patent Literature 1. FIG. 3 is a diagram that has a horizontal axis representing an amplitude value [mm] and a vertical axis representing a response time [sec], and shows investigated response times taken until viscosity values became stabilized (judged when the viscosity value reached 1% or less of a unit displayed on the display by way of example) at respective amplitude values when standard solutions of 1 [mPa·s], 1000 [mPa·s], 8000 [mPa·s], and 26000 [mPa·s] were used as samples, and 45 [ml] each of the samples were measured under fixed conditions at a measurement temperature of 25° C. while the target amplitude value was changed to 0.07, 0.10, 0.20, and 1.2 [mm]. FIG. 3 proves that when the viscosity of the sample is high or the amplitude value is small, the response speed is low. In particular, in a case where the viscosity of the sample is as high as 26000 [mPa·s] and the amplitude value is as small as 0.07 [mm], a response time as long as approximately 55 [sec] is taken. A possible cause for this is that, in a case where the sample has a high viscosity, it puts a high load on a mechanical system of the device, and an output signal obtained at a low amplitude value is small.

Next, FIG. 4 is a measurement graph obtained with the tuning fork vibration viscometer of Patent Literature 1. FIG. 4 shows temporal changes in viscosity value obtained when 45 [ml] of a commercially available body cream used as a sample was measured under fixed conditions at a measurement temperature of 25° C. while the target amplitude value was changed to 0.07, 0.10, 0.20, 0.4, 0.6, 0.8, 1.0, and 1.2 [mm]. As described above, in a low amplitude range, the response speed is low, and therefore, when observing the temporal changes, the viscosity value wildly rises and falls. When the response speed is thus low, particularly in a case of measurement including fine changes in shear rate, a problem occurs in which a continuous smooth measurement graph cannot be obtained.

Disturbance of a feedback system of a viscometer is a viscosity of a sample, however, for viscometers, most measuring objects are non-Newtonian fluids. Non-Newtonian fluids change in viscosity every second according to the amplitude, therefore, a feedback gain completely differs by measurement, and it is difficult to make gain setting in a table in advance. Therefore, the tuning fork vibration viscometer described in Patent Literature 1 performs measurement at a constant feedback gain (0 [dB]) of a feedback system regardless of a viscosity of a sample and a set amplitude value.

This is not only in the case of the tuning fork vibration viscometer. It is known that even in other viscometers, a feedback system is also configured based on an input value of a set target shear rate and an output value from a mechanical system dunked in a sample, and measurement is performed with a configuration where an output becomes stabilized, therefore, for the same reason, the response speed is low in a range of high viscosity or low shear rate, and a continuous smooth graph cannot be obtained.

In order to solve the problem in the conventional techniques, the present invention, in relation to measurement of viscosity of a fluid, particularly, provides a method and device for improving a response speed in measurement in a range of high viscosity and/or low shear rate (low amplitude, low rotation) and obtaining a continuous smooth measurement graph (like an analog graph).

Means for Solving the Problems

In order to solve the above-described object, according to an aspect of the present invention, a tuning fork vibration viscometer includes a pair of vibrators to be dunked in a sample, an electromagnetic drive for vibrating the vibrators, an amplitude value changing means for outputting a target amplitude value of the vibrators, and a displacement detection sensor for measuring an amplitude of the vibrators, and performs feedback control for controlling a driving current applied to the electromagnetic drive so that an output value of the displacement detection sensor corresponds to the target amplitude value and measures viscosity of the sample based on a value of the driving current, wherein the tuning fork vibration viscometer further includes a gain control means that sets a feedback gain in the feedback control high at first, in a state of a specific target amplitude value with respect to a sample having a specific viscosity, reduces the gain until a limiting point that is just before a measured value of viscosity value starts oscillating is found, defines the gain at the limiting point as an optimum feedback gain, so as to perform a measurement of the viscosity by using the optimum feedback gain, and performs the measurement every time the target amplitude value is changed.

Alternatively, a method of measuring a property of a sample by utilizing a tuning fork vibration viscometer that includes a pair of vibrators to be dunked in a sample, an electromagnetic drive for vibrating the vibrators, an amplitude value changing means for outputting a target amplitude value of the vibrators, and a displacement detection sensor for measuring an amplitude of the vibrators, and performs feedback control for controlling a driving current applied to the electromagnetic drive so that an output value of the displacement detection sensor corresponds to the target amplitude value and measures viscosity of the sample based on a value of the driving current, includes: setting a feedback gain high at first in the feedback control in a state of a specific target amplitude value with respect to a sample having a specific viscosity, reducing the gain until a limiting point that is just before a measured value of viscosity starts oscillating is found, defining the gain at the limiting point as an optimum feedback gain, so as to perform a measurement of the viscosity by using the optimum feedback gain, and performing the measurement every time the target amplitude value is changed.

Alternatively, a viscometer includes a machine part to be dunked in a sample for generating a shear rate of the sample, a machine drive for moving the machine part, a shear rate changing means for outputting a target shear rate of the machine part, and a displacement detection sensor for measuring a displacement of the machine part, and performs feedback control for controlling a driving force of the machine drive so that an output value of the displacement detection sensor corresponds to the target shear rate and measures viscosity of the sample based on a value of the driving force, wherein the viscometer further includes a gain control means that sets a feedback gain in the feedback control high at first, in a state of a specific target shear rate with respect to a sample having a specific viscosity, reduces the gain until a limiting point that is just before a measured value of viscosity starts oscillating is found, defines the gain at the limiting point as an optimum feedback gain, so as to perform a measurement of the viscosity by using the optimum feedback gain, and performs the measurement every time the target shear rate is changed.

Alternatively, a method of measuring a property of a sample by utilizing a viscometer that includes a machine part to be dunked in a sample for generating a shear rate of the sample, a machine drive for moving the machine part, a shear rate changing means for outputting a target shear rate of the machine part, and a displacement detection sensor for measuring a displacement of the machine part, and performs feedback control for controlling a driving force of the machine drive so that an output value of the displacement detection sensor corresponds to the target shear rate, and measures viscosity of the sample on a value of the driving force, includes: setting a feedback gain high at first in the feedback control in a state of a specific target shear rate with respect to a sample having a specific viscosity, reducing the gain until a limiting point that is just before a measured value of viscosity starts oscillating is found, defining the gain at the limiting point as an optimum feedback gain, so as to perform a measurement of the viscosity by using the optimum feedback gain, and performing the measurement every time the target shear rate is changed.

According to this aspect, an optimum feedback gain can be set for each measurement, therefore, the response speed becomes stabilized in any measurement of a specific viscosity at a specific shear rate (even in a measurement in a range of high viscosity and/or low shear rate), resulting in obtaining a continuous smooth measurement graph.

According to another aspect of the present invention, a tuning fork vibration viscometer includes a pair of vibrators to be dunked in a sample, an electromagnetic drive for vibrating the vibrators, an amplitude value changing means for outputting a target amplitude value of the vibrators, and a displacement detection sensor for measuring an amplitude of the vibrators, and performs feedback control for controlling a driving current applied to the electromagnetic drive so that an output value of the displacement detection sensor corresponds to the target amplitude value and measures viscosity of the sample based on a value of the driving current, wherein the tuning fork vibration viscometer further includes a simple feedback setting means for changing a feedback gain in the feedback control in a plurality of stages in an oscillation field or below according to a target amplitude value output from the amplitude value changing means by calculating in advance, as the oscillation field, a plot field of optimum feedback gains with respect to target amplitude values, obtained through a test conducted in a plurality of patterns using the plurality of target amplitude values in which a sample having a specific viscosity is measured at a specific target amplitude value, and an optimum feedback gain is obtained in the feedback control at a limiting point that is just before an obtained viscosity value oscillates.

Alternatively, a method of measuring a property of a sample by utilizing a tuning fork vibration viscometer that includes a pair of vibrators to be dunked in a sample, an electromagnetic drive for vibrating the vibrators, an amplitude value changing means for outputting a target amplitude value of the vibrators, and a displacement detection sensor for measuring an amplitude of the vibrators, and performs feedback control for controlling a driving current applied to the electromagnetic drive so that an output value of the displacement detection sensor corresponds to the target amplitude value and measures viscosity of the sample based on a value of the driving current, includes performing a test in which a sample having a specific viscosity is measured under a specific target amplitude value and an optimum feedback gain in the feedback control at a limiting point that is just before an obtained viscosity value oscillates, and calculating in advance, as an oscillation field, a plot field of optimum feedback gains with respect to target amplitude values, obtained through the test conducted in a plurality of patterns using the plurality of target amplitude values, and changing a feedback gain in the feedback control in a plurality of stages in the oscillation field or below according to a target amplitude value output from the amplitude value changing means.

Alternatively, a viscometer includes a machine part to be dunked in a sample for generating a shear rate of the sample, a machine drive for moving the machine part, a shear rate changing means for outputting a target shear rate of the machine part, and a displacement detection sensor for measuring a displacement of the machine part, and performs feedback control for controlling a driving force of the machine drive so that an output value of the displacement detection sensor corresponds to the target shear rate and measuring viscosity of the sample based on a value of the driving force, wherein the viscometer further includes a simple feedback setting means for changing a feedback gain in the feedback control in a plurality of stages in an oscillation field or below according to a target shear rate output from the shear rate changing means by calculating in advance, as the oscillation field, a plot field of optimum feedback gains with respect to target shear rates, obtained through a test conducted in a plurality of patterns using the plurality of target shear rates in which a sample having a specific viscosity is measured at a specific target shear rate, and an optimum feedback gain is obtained in the feedback control at a limiting point that is just before an obtained viscosity value oscillates.

Alternatively, a method of measuring a property of a sample by utilizing a viscometer that includes a machine part to be dunked in a sample for generating a shear rate of the sample, a machine drive for moving the machine part, a shear rate changing means for outputting a target shear rate of the machine part, and a displacement detection sensor for measuring a displacement of the machine part, and performs feedback control for controlling a driving force of the machine drive so that an output value of the displacement detection sensor corresponds to the target shear rate, and measures viscosity of the sample based on a value of the driving force, includes performing a test in which a sample having a specific viscosity is measured under a specific target shear rate and an optimum feedback gain in the feedback control at a limiting point that is just before an obtained viscosity value oscillates, and calculating in advance, as an oscillation field, a plot field of optimum feedback gains with respect to target shear rates, obtained through the test conducted in a plurality of patterns using the plurality of target shear rates, and changing a feedback gain in the feedback control in a plurality of stages in the oscillation field or below according to a target shear rate output from the shear rate changing means.

According to this aspect, a test is conducted in a plurality of patterns using the plurality of target shear rates covering combinations of viscosities and shear rates expected to be measured, and based on optimum feedback gains of these tests, an oscillation field is calculated in advance, and at the time of measurement, a feedback gain is changed in a plurality of stages (a simple feedback gain is set) in the oscillation field or below depending on a target shear rate (target amplitude value), and accordingly, a preferable gain can be set in any measurement (from low viscosities to high viscosities) based on a known and controllable target shear rate (target amplitude value), therefore, by a simple configuration, a response speed becomes stabilized in any measurement (even in measurement in ranges of high viscosities and/or low shear rates), resulting in obtaining a continuous smooth measurement graph.

Effects of the Invention

According to the present invention, a response speed of measurement particularly in a range of high viscosity and low shear rate is improved, and a continuous (analog) smooth measurement graph can be obtained.

EMBODIMENTS FOR IMPLEMENTING INVENTION

Next, preferred embodiments of the present invention are described.

First Embodiment (Device Configuration of First Embodiment)

A first embodiment is a tuning fork vibration viscometer. The configuration of a drive mechanical part 2 of a tuning fork vibration viscometer described in Patent Literature 1 shown in FIG. 1 is common to a tuning fork vibration viscometer 1 according to the first embodiment. The detailed configuration of the main body of the tuning fork vibration viscometer 1 and the drive mechanical part 2 is also described in, for example, JPA 2005-9862.

Vibrators 3 and 3 are a pair of machine parts to be dunked in a sample 4 and generate a shear rate in the sample 4, and are formed of thin tabular plate members of ceramic members, metal members, or the like, and have circular enlarged portions provided at their tip ends. The enlarged portions are portions to come into liquid-contact with the sample 4. The vibrators 3 and 3 are configured so that their central axes in the thickness directions are positioned on the same plane inside the sample 4.

The symbols 5 and 5 denote a pair of leaf springs, and base end portions of the vibrators 3 and 3 are fixed to the leaf springs 5 and 5 via connecting members 6 and 6. End portions on the opposite sides of the vibrator connecting side end portions of the leaf springs 5 are fixed to right and left projecting portions of a frame 7 having a reverse convex shape. At longitudinal central portions of the leaf springs 5, thin portions are formed. The frame 7 is supported by a stand, not shown, of the main body of the viscometer 1, and is configured so as to be movable up and down and forward and backward by operations of a handle provided on the main body. Accordingly, the pair of vibrators 3 and 3 are dunked to a predetermined depth in the sample 4. At the downward convex portion of the frame 7, a sample temperature sensor 8 is provided.

The symbol 10 denotes an electromagnetic drive, and is configured as a moving magnet system in which one end portion of a ferrite magnet 10a fixed to a central portion of the connecting member 6 connected to the vibrator 3 is inserted inside an electromagnetic coil 10b fixed to a side surface of the downward convex portion of the frame 7. By forcibly vibrating the leaf springs 5 and 5 in opposite phases at a fixed frequency by the electromagnetic drive 10, the vibrators 3 and 3 vibrate in the same manner. The symbol 11 denotes an eddy current loss detecting non-contact displacement detection sensor. On the assumption that an amplitude of the vibrator 3 is equivalent to an amplitude of the leaf spring 5 integrated with the vibrator 3, the displacement detection sensor 11 is fixed to the frame 7 at a position in proximity to the vibrator connecting side end portion of the leaf spring 5, and detects the amplitude of the leaf spring 5.

(Control Configuration of First Embodiment)

Next, FIG. 5 is a block diagram of a control system of the tuning fork vibration viscometer 1 according to the first embodiment. The tuning fork vibration viscometer according to the first embodiment includes a sine wave generating circuit 13, a comparator 14, a controller 15, an I/V converter 16, an A/D converter 17, and a microcontroller 18. A PWM modulation circuit 12A for changing a target amplitude value and a PWM modulation circuit 12B for changing a feedback gain are connected to (or incorporated in) the microcontroller 18. Between the PWM modulation circuit 12A and the comparator 14, an amplitude value D/A converter 31 that D/A converts an amplitude control signal relating to a target amplitude value is connected. Between the PWM modulation circuit 12B and the controller 15, a gain D/A converter 32 that D/A converts a gain control signal described later is connected. The microcontroller 18 and the PWM modulation circuit 12A serve as amplitude value changing means.

To the microcontroller 18, a display 22 that numerically displays measured values and an exclusive controller 24 that has an input part, and makes a graph of the measured values, separate from the main body of the tuning fork vibration viscometer 1, are connected, and a user can set measurement conditions from the exclusive controller 24. The measurement conditions are a pattern of changing the amplitude of the vibrators 3 and 3 (a lower limit value and an upper limit value of the amplitude, an amount of change in amplitude, and whether the amplitude is to be raised, lowered, or changed in a reciprocating manner), etc. By the exclusive controller 24, various graphic forms such as a temporal change graph of a measured value and a flow curve showing a relationship between an amplitude value and a viscosity value, etc., can be displayed according to settings.

When a measurement is started, a drive signal is output from the microcontroller 18 to the sine wave generating circuit 13, and through the I/V converter 16, a driving current flows into the electromagnetic coil 10b. Accordingly, magnetic force is generated at the electromagnetic drive 10, and the vibrators 3 and 3 start to resonantly vibrate in opposite phases. An amplitude of the vibrators 3 responsive to the resonant vibration is detected by the displacement detection sensor 11 and output to the comparator 14.

The microcontroller 18 outputs an amplitude control signal corresponding to a target amplitude value according to measurement conditions to the comparator 14 via the PWM modulation circuit 12A. The comparator 14 compares the target amplitude value with an input value from the displacement detection sensor 11, and transmits a signal to the controller 15. The microcontroller 18 sets an initial value of a gain of a gain control part 33 based on a gain control signal, and reduces the gain by observing oscillation of the viscosity value as described later (Steps S103 to S105 in FIG. 6). The controller 15 includes the gain control part 33 configured to include a variable amplifier, and a PID control part 15A. The gain control part 33 multiplies the signal from the comparator 14 by a feedback gain set based on the gain control signal, and outputs a multiplication result to the PID control part 15A. The PID control part 15A performs feedback control by increasing or decreasing a driving current to be applied to the electromagnetic coil 10b so that the vibrators 3 and 3 vibrate at the target amplitude value. The microcontroller 18, the PWM modulation circuit 12B, and the gain control part 33 serve as gain control means.

A driving current applied to the electromagnetic coil 10b is sampled at a preset timing. Then, this driving current is input into the microcontroller 18 via the I/V converter 16 and the A/D converter 17, converted into a corresponding viscosity value by the microcontroller 18, and displayed by the display 22 and the exclusive controller 24. A signal from the sample temperature sensor 8 is input into the microcontroller 18 via the temperature A/D converter 19, and displayed by the display 22 and the exclusive controller 24 as necessary.

(Measuring Method of First Embodiment)

Next, a method of measuring a property of a sample by the tuning fork vibration viscometer according to the first embodiment, including a gain control method, is described. FIG. 6 is a flowchart showing a method of measuring a property of a sample by the tuning fork vibration viscometer 1 according to the first embodiment.

First, the process advances to Step S101, and according to set measurement conditions, a target amplitude value is set. Next, the process advances to Step S102, and the vibrators 3 and 3 are started to vibrate. Next, in Step S103, the microcontroller 18 outputs a gain control signal to the gain control part 33, and sets a predetermined high feedback gain. Next, in Step S104, whether or not a viscosity value obtained at the set gain oscillates is checked. Whether or not the viscosity value oscillates is checked based on, by way of example, whether the viscosity value is 10% or more of a unit displayed on the display when the viscosity value is sampled twice [per second]. The judgment as to whether or not the viscosity value oscillates (setting of a limiting point) may be preferably designed based on measurement accuracy and a measurement time required for the device. When the viscosity value oscillates, the process advances to Step S105, and after the previous gain is reduced by preset ΔdB, the process returns to Step S104. When the viscosity value does not oscillate, it is judged that a limiting point just before the viscosity value oscillates is found, and the process advances to Step S106, and the current gain is established as an optimum feedback gain $FG_{OP}$. Next, the process advances to Step S107, and the viscosity value obtained at the optimum feedback gain $FG_{OP}$ is acquired as a measured value of viscosity at the value of this target amplitude value, and this measured value is displayed on the display 22, and displayed in a graphic form by the exclusive controller 24. Next, the process advances to Step S108, and the target amplitude value is changed to a next target amplitude value, and this processing is repeated until the measurement conditions are completed.

(Response Speed of First Embodiment)

FIG. 7 is a diagram showing a response speed of the tuning fork vibration viscometer 1 according to the first embodiment. FIG. 7 represents the amplitude value [mm] on the horizontal axis and the response time [sec] on the vertical axis, and shows investigated response times taken until viscosity values became stabilized (judged when the viscosity value reached 1% or less of a unit displayed on the display by way of example) at respective amplitude values when standard solutions of 1 [mPa·s], 1000 [mPa·s], 8000 [mPa·s], and 26000 [mPa·s] were used as samples 4 and 45 [ml] each of these were measured under fixed conditions at a measurement temperature of 25° C. while the target amplitude value was changed to 0.07, 0.10, 0.20, and 1.2 [mm]. FIG. 7 proves that, in the first embodiment, the response time is within approximately 15 [sec] in any measurement in ranges of low to high viscosities and low to high amplitudes.

Based on this, according to the first embodiment, the response speed became higher in each range (even in high-viscosity ranges and low-viscosity ranges), therefore, even if setting is made to finely change the amplitude (the amount of change in amplitude value is set to be small), no wild rises and falls are observed even with the data of temporal changes, and a continuous smooth measurement graph can be obtained. In addition, according to the first embodiment, the response speed becomes higher particularly in measurement in the range of high viscosity and low amplitude (low shear rate range), and accordingly, an overall measurement time is greatly shortened.

Second Embodiment (Device Configuration of Second Embodiment)

The second embodiment is also a tuning fork vibration viscometer, however, it has a concept of gain setting different from that of the first embodiment, and adopts a method and control configuration different from those of the first embodiment. The configuration of a drive mechanical part 2 of a tuning fork vibration viscometer 1 according to the second embodiment is similar to the first embodiment (FIG. 1).

(Control Configuration of Second Embodiment)

Next, FIG. 8 is a block diagram of a control system of the tuning fork vibration viscometer 1 according to the second embodiment, and FIG. 9 is a detailed circuit diagram of an essential portion of FIG. 8. It is to be noted that the same components as in the first embodiment (FIG. 5) are designated by the same symbols, and description thereof is omitted appropriately.

As in the first embodiment, the microcontroller 18 and the PWM modulation circuit 12A serve as amplitude value changing means. In the second embodiment, the configuration of the controller 15 is different. The controller 15 includes a gain setting part 34 including a selection circuit 34A having different resistance values R1, R2, . . . , Rn and an amplifier 34B, and a PID control part 15A. The gain setting part 34 operates when any one of the resistance values R1, R2, . . . , Rn is selected according to ON/OFF of analog switches SW1, SW2, . . . , SWn respectively connected to and paired with the resistance values R1, R2, . . . Rn. The analog switches SW1, SW2, . . . , SWn operate in response to a gain selection signal output by the microcontroller 18. The gain setting part 34 multiplies a signal from a comparator 14 by a simple feedback gain $FG_{sim}$=Rn/R0 (R0: resistance value of a resistor connected between the comparator 14 and the gain setting part 34) set according to the gain selection signal, and outputs a multiplication result to the PID control part 15A. Which simple feedback gain $FG_{sim}$ the microcontroller 18 selects is determined from an oscillation field $P_{OS}$ described next. The microcontroller 18 and the gain setting part 34 serve as simple feedback gain setting means.

(Oscillation Field)

An oscillation field $P_{OS}$ is a plot field of optimum feedback gains $FG_{OP}$ with respect to target amplitude values, obtained by conducting a test in advance in a plurality of patterns using the plurality of target amplitude values in which a sample having a specific viscosity at a specific target amplitude value is measured and an optimum feedback gain $FG_{OP}$ in feedback control at a limiting point just before an obtained viscosity value oscillates obtained by using a specific tester that includes a pair of vibrators to be dunked in a sample, an electromagnetic drive for vibrating the vibrators, an amplitude value changing means for outputting a target amplitude value of the vibrators, and a displacement detection sensor for measuring an amplitude of the vibrators, and can perform feedback control to control a driving current to be applied to the electromagnetic drive so that an output value of the displacement detection sensor corresponds to the above-described target amplitude value.

As examples of a tester and a testing method to obtain the oscillation field $P_{OS}$, the device (FIG. 5) and the measuring method (FIG. 6) of the first embodiment can be used. However, the tester and testing method to obtain the oscillation field $P_{OS}$ are only required to obtain data just before a measured value oscillates, and are not limited to those of the first embodiment. For example, the optimum feedback gain $FG_{OP}$ can also be obtained by obtaining gain characteristics and phase characteristics of a system including the above-described mechanical system and electric system by sweeping a frequency with a device having the system.

In detail, FIG. 10 is a diagram showing an example of an oscillation field $P_{OS}$. FIG. 10 plots, by representing an amplitude value [mm] on the horizontal axis and an optimum feedback gain $FG_{OP}$ [dB] on the vertical axis, respective optimum feedback gains $FG_{OP}$ [dB] obtained when standard solutions of 1 [mPa·s], 1000 [mPa·s], 8000 [mPa·s], and 26000 [mPa·s] were used as samples 4 and 45 [ml] each of the samples were measured under fixed conditions at a measurement temperature of 25° C. while a target amplitude value was changed to 0.07, 0.10, 0.20, and 1.2 [mm].

Thus, by conducting a test in advance in a plurality of patterns using a plurality of target amplitude values covering combinations of viscosities and amplitudes expected to be measured (test in which amplitude changes from low amplitudes to high amplitudes expected to be measured are applied to respective fluids with viscosities from low to high viscosities expected to be measured), optimum feedback gains $FG_{OP}$ of these are obtained, and a plot field of the obtained optimum feedback gains $FG_{OP}$ (the field below the line (the alternate long and short dashed line in FIG. 10) connecting maximum values with respect to respective target amplitude values) is obtained as an oscillation field $P_{OS}$. That is, the shaded portion in FIG. 10 is the oscillation field $P_{OS}$.

(Method of Setting Simple Feedback Gain)

A simple feedback gain $FG_{sim}$ is set to change in a plurality of stages according to a target amplitude value in the oscillation field $P_{OS}$ or below. FIG. 11 shows an example of setting of the simple feedback gain $FG_{sim}$. FIG. 11 shows an example, in a case where the oscillation field $P_{OS}$ shown in FIG. 10 is obtained through the test conducted in advance, based on the values of this oscillation field $P_{OS}$, the simple feedback gain $FG_{sim}$ is set to 14 [dB] during measurement at a target amplitude value of 0 to 0.2 [mm], the simple feedback gain $FG_{sim}$ is set to 5 [dB] during measurement at a target amplitude value of more than 0.2 to 0.4 [mm], and the simple feedback gain $FG_{sim}$ is set to 0 [dB] during measurement at a target amplitude value of more than 0.4 [mm]. The numerical values and number of stages in FIG. 11 are shown by way of example.

That is, in the second embodiment, based on a controllable and to-be-known target amplitude value, a simple feedback gain $FG_{sim}$ that preferably functions in any measurement (from low viscosity to high viscosity) is set in stages. The simple feedback gain $FG_{sim}$ suffices to change in a plurality of stages to a gain (1), a gain (2), . . . , a gain (n) in the oscillation field $P_{OS}$ or below according to a target amplitude value. From these set simple feedback gains $FG_{sim}$, resistance values R1, R2, . . . , Rn are determined, and at the time of measurement, by using the switches SW1, SW2, . . . , SWn, the microcontroller 18 selectively sets a gain corresponding to a target amplitude value.

(Measuring Method of Second Embodiment)

Next, a method of measuring a property of a sample by the tuning fork vibration viscometer 1 according to the second embodiment in a case where the simple feedback gain $FG_{sim}$ is set as shown in the example of FIG. 11 is described. FIG. 12 is a flowchart showing a method of measuring a property of a sample by the tuning fork vibration viscometer according to the second embodiment.

First, the process advances to Step S201, and according to set measurement conditions, a target amplitude value is set. Next, the process advances to Step S202, and whether the set target amplitude value is not more than 0.2 [mm] is judged. When the set target amplitude value is not more than 0.2 [mm], the process advances to Step S203, and the gain (1), the simple feedback gain $FG_{sim}$ in this case, is set to 14 [dB]. Next, the process advances to Step S207, and the vibrators 3 and 3 are started to vibrate. On the other hand, when the target amplitude value is more than 0.2 [mm] in Step S202, the process advances to Step S204, and whether the set target amplitude value is not more than 0.4 [mm] is judged. When the target amplitude value is not more than 0.4 [mm], the process advances to Step S205, and the gain (2), the simple feedback gain $FG_{sim}$ in this case, is set to 5 [dB], the process advances to Step S207, and the vibrators 3 and 3 are started to vibrate. When the target amplitude value is more than 0.4 [mm] in Step S204, the process advances to Step S206, and the gain (3), the simple feedback gain $FG_{sim}$ in this case, is set to 0 [dB], the process advances to Step S207, and the vibrators 3 and 3 are started to vibrate. When the vibrators 3 and 3 are started to vibrate in Step S207, next, the process advances to Step S208, and a viscosity value obtained at the set simple feedback gain $FG_{sim}$ is acquired as a measured value of viscosity at the time of this target amplitude value, and this measured value is displayed on the display 22 and displayed in a graphic form by the exclusive controller 24. Next, the process advances to Step S208, the target amplitude value is changed to a next target amplitude value, and the process returns to Step S201, and this processing is repeated until the measurement conditions are completed.

(Response Speed of Second Embodiment)

FIG. 13 is a diagram showing a response speed of the tuning fork vibration viscometer according to the second embodiment. FIG. 13 represents the amplitude value [mm] on the horizontal axis and the response time [sec] on the vertical axis, and shows investigated response times taken until viscosity values became stabilized (judged when the viscosity value reached 1% or less of a unit displayed on the display by way of example) at respective amplitude values when standard solutions of 1 [mPa·s], 1000 [mPa·s], 8000 [mPa·s], and 26000 [mPa·s] were used as samples 4 and 45 [ml] each of these were measured under fixed conditions at a measurement temperature of 25° C. while the target amplitude value was changed to 0.07, 0.10, 0.20, and 1.2 [mm]. FIG. 13 proves that, in the second embodiment, the response time is within approximately 25 [sec] in any measurement in ranges of low to high viscosities and low to high amplitudes.

Based on this, according to the second embodiment, the response speed became higher in each range (even in high-viscosity ranges and low-viscosity ranges), therefore, even if setting is made to finely change the amplitude (the amount of change in amplitude value is set to be small), no wild rises and falls are observed even with the data of temporal changes, and a continuous smooth measurement graph can be obtained. In addition, according to the second embodiment, the response speed becomes higher particularly in measurement in the range of high viscosity and low amplitude (low shear rate range), and accordingly, an overall measurement time is greatly shortened.

Example

FIG. 14 and FIG. 15 are measurement graphs obtained with the tuning fork vibration viscometer 1 according to the second embodiment when 45 [ml] of a commercially available hand cream used as a sample 4 was measured under fixed conditions at a measurement temperature of 25° C. while the target amplitude value was changed to rise and then lower by changing the value between 0.07 to 1.20 [mm] in increments/decrements of 0.01 [mm] (227 [steps]). FIG. 14 represents time [sec] on the horizontal axis, the amplitude value [mm] on the right vertical axis, and the viscosity value [mPa·s] on the left vertical axis, and FIG. 15 represents the amplitude value [mm] on the horizontal axis and the viscosity value [mPa·s] on the vertical axis.

As can be found in FIG. 14 and FIG. 15, according to the second embodiment, first, the response speed became higher in each range, therefore, even if the amplitude is finely changed (in increments/decrements of 0.01 [mm] (227 [steps])), a continuous smooth measurement graph in which no wild rises and falls are observed with the data can be obtained.

Second, since the response speed became higher in each range, an overall measurement time can be shortened. In detail, for example, when a measurement is attempted by using the conventional tuning fork vibration viscometer (Patent Literature 1) in which the amplitude is changed in increments/decrements of 0.01 [mm] (227 [steps]) as in the case of the measurement conditions of FIG. 14 and FIG. 15, in consideration of the response speed results shown in FIG. 3, waiting for approximately 55 [sec] for stabilization+5 [sec] for data acquirement design can be considered as acquirement of a measured value. The measurement time is as long as approximately 3.4 hours. On the other hand, an example in which the tuning fork vibration viscometer 1 according to the second embodiment was used and the amount of change in amplitude was set to be small (the amplitude was changed in increments/decrements of 0.01 [mm], that is, 227 [steps]) is shown in FIG. 14 and FIG. 15, and in this example, the response speed in each range became higher due to simple gain setting, and the system became stabilized earlier due to the small amount of change in amplitude, so that waiting for approximately 10 [sec] for stabilization+2 [sec] for data acquirement design could be realized as acquirement of a measured value of viscosity in Step S208. As a result, the measurement finished in 45 minutes.

In addition, in the second embodiment, a gain change uses hardware elements such as switches SW1, SW2, . . . , SWn, and this is simple in configuration, therefore, the device cost can be reduced.

Third Embodiment

In a third embodiment, the measuring method according to the first embodiment is performed with a rotational viscometer. FIG. 16 is a block diagram of a control system of a rotational viscometer according to the third embodiment.

(Device and Control Configuration of Third Embodiment)

It is to be noted that components (as essential functions) common to the components of the first embodiment are designated by the same symbols. A rotational viscometer (cone plate type, coaxial double cylinder type) according to the third embodiment includes a rotor (machine part) 3 to be dunked in a sample 4 and generates a shear rate, and for driving this rotor 3, an actuator (machine drive) 13 that rotates the rotor 3, a comparator 14, a controller 15, a microcontroller 18, a displacement detection sensor 11 such as a rotary encoder that detects rotation (displacement) of the rotor 3, and a torque detection sensor 110 such as a torsion spring that detects a torque of the rotor 3. The controller 15 includes a gain control part 33 and a PID control part 15A. To the microcontroller 18, a display and an input part, etc., not shown, are connected, and the microcontroller 18 determines a target shear rate (rotation speed [rpm]) of the rotor 3 according to measurement conditions and outputs a shear rate control signal corresponding to the target shear rate to the comparator 14, and controls the actuator 13. The microcontroller 18 serves as a shear rate changing means.

A rotation speed of the rotor 3 is detected by the displacement detection sensor 11 and output to the comparator 14. The comparator 14 compares a target shear rate with an input value from the displacement detection sensor 11, and transmits a signal to the controller 15. The microcontroller 18 sets an initial value of a gain of the gain control part 33 according to a gain control signal, and reduces the gain by observing oscillation of a viscosity value as described later (Steps S103 to S105 in FIG. 17). The controller 15 multiplies the signal from the comparator 14 by a feedback gain set according to the gain control signal in the gain control part 33, and outputs a multiplication result to the PID control part 15A. The PID control part 15A performs feedback control by increasing/decreasing a driving force of the actuator 13 so that the rotor 3 rotates at the target shear rate. The microcontroller 18, the PWM modulation circuit 12B, and the gain control part 33 serve as gain control means. On the other hand, a torque applied to the rotor 3 is detected by the torque detection sensor 110 and output to the microcontroller 18. The microcontroller 18 converts the detected torque into a corresponding viscosity value by utilizing a proportional relationship between the torque and the sample viscosity, and displays the viscosity value on the display.

(Measuring Method of Third Embodiment)

FIG. 17 is a flowchart showing a method of measuring a property of a sample by the rotational viscometer according to the third embodiment. The measuring method according to the third embodiment is substantially the same as the measuring method according to the first embodiment, therefore, the step numbers of the first embodiment are used in common and different portions are replaced and described. First, when the process advances to Step S101, a target shear rate is set according to set measurement conditions. Next, when driving of the rotor 3 is started in Step S102, a high feedback gain is set at first in Step S103. Next, when it is judged that a viscosity value oscillates in Step S104, the process advances to Step S105, and the gain is reduced until a limiting point is found. When a limiting point is found, an optimum feedback gain $FG_{OP}$ is established in Step S106, and a viscosity value at the time of this target shear rate is acquired as a measured value, and this measured value is displayed on the display and displayed in a graphic form. Next, in Step S108, the target shear rate is changed to a next target shear rate, and this processing is repeated until the measurement conditions are completed.

Fourth Embodiment

In a fourth embodiment, the measuring method according to the second embodiment is performed with a rotational viscometer. FIG. 18 is a block diagram of a control system of a rotational viscometer according to the fourth embodiment.

(Device and Control Configuration of Fourth Embodiment)

A viscometer according to a fourth embodiment has the same device configuration as the viscometer according to the third embodiment, and includes a rotor (machine part) 3, an actuator (machine drive) 13, a comparator 14, a controller 15, a microcontroller 18, a displacement detection sensor 11, and a torque detection sensor 110. The controller 15 includes a gain setting part 34 including a selection circuit 34A having resistance values R1, R2, . . . , Rn different from each other and arranged in descending order and an amplifier 34B, and a PID control part 15A. The microcontroller 18 outputs a shear rate control signal relating to a target shear rate to the comparator 14, and controls the actuator 13. The microcontroller 18 serves as a shear rate changing means.

A rotation speed of the rotor 3 is detected by the displacement detection sensor 11 and output to the comparator 14. The comparator 14 compares a target shear rate with an input value from the displacement detection sensor 11, and transmits a signal to the controller 15. The controller 15 multiplies the signal from the comparator 14 by a simple feedback gain $FG_{sim}=Rn/R0$ set according to a gain selection signal in the gain setting part 34, and outputs a multiplication result to the PID control part 15A. Which simple feedback gain $FG_{sim}$ the microcontroller 18 selects is determined from an oscillation field $P_{OS}$. The microcomputer 18 and the gain setting part 34 serve as simple feedback gain setting means.

(Method of Setting Simple Feedback Gain)

Also in the fourth embodiment, as an oscillation field $P_{OS}$, by conducting a test in advance in a plurality of patterns using a plurality of target shear rates covering combinations of viscosities and shear rates expected to be measured (test in which shear rate changes from low shear rates to high shear rates are applied to respective fluids with viscosities from low to high viscosities), optimum feedback gains $FG_{OP}$ of these are obtained, and a plot field of the obtained optimum feedback gains $FG_{OP}$ (the field below the line connecting maximum values with respect to respective target shear rates) is obtained. The simple feedback gain $FG_{sim}$ is set to a plurality of gains of a gain (1), a gain (2), . . . , a gain (n) in stages in the oscillation field $P_{OS}$ or below according to the target shear rate.

(Measuring Method of Fourth Embodiment)

FIG. 19 is a flowchart showing a method of measuring a property of a sample by the rotational viscometer according to the fourth embodiment. The measuring method of the fourth embodiment is substantially the same as the measuring method of the second embodiment, therefore, the step numbers in the second embodiment are used in common, and different portions are replaced and described. First, the process advances to Step S201, and according to set measurement conditions, a target shear rate is set. Next, the process advances to Step S202, and whether the set target shear rate is not more than A [rpm] is judged, and when the set target shear rate is not more than A [rpm], the process advances to Step S203, and the simple feedback gain $FG_{sim}$ (1) is set, and the process advances to Step S207. On the other hand, when the set target shear rate is higher than A [rpm], the process advances to Step S204 and whether the set target shear rate is not more than B [rpm] is judged. When it is not more than B [rpm], the process advances to Step S205, the simple feedback gain $FG_{sim}$ (2) is set, and the process advances to Step S207. On the other hand, when the set target shear rate is higher than B [rpm], the process advances to Step S206, the simple feedback gain $FG_{sim}$ (3) is set, and the process advances to Step S207, and the rotor 3 is started to rotate. Next, in Step S208, a viscosity value obtained at the set simple feedback gain $FG_{sim}$ is acquired as a measured value of viscosity at the time of this target shear rate, and this measured value is displayed on the display and displayed in a graphic form. Next, in Step S209, the target shear rate is changed to a next target shear rate, and this processing is repeated until the measurement conditions are completed. It is to be noted that, quoting the second embodiment, the simple feedback gain $FG_{sim}$ is set in three stages in the description given above, however, the simple feedback gain $FG_{sim}$ may be set in a plurality of stages in the oscillation field $P_{OS}$ or below.

Embodiments of the method and device according to the present invention are described above by adopting tuning fork vibration viscometers and rotational viscometers, however, the measuring method according to the present invention can also be realized with other viscometers having a configuration in which a feedback system is configured based on an input value of a set target shear rate and an output value from a mechanical system to be dunked in a sample, and a measured value is obtained when the output becomes stabilized.

With the method and device according to the present invention, a continuous (analog) smooth measurement graph can be obtained, therefore, an effect is obtained in which an inflection point can be easily grasped. This leads to an improvement in measurement accuracy such as yield value that becomes an index of a property of a sample, so that the method and device according to the present invention can contribute to a clarification of a property of a fluid, closer to the actual condition.

DESCRIPTION OF SYMBOLS

Figure 1:
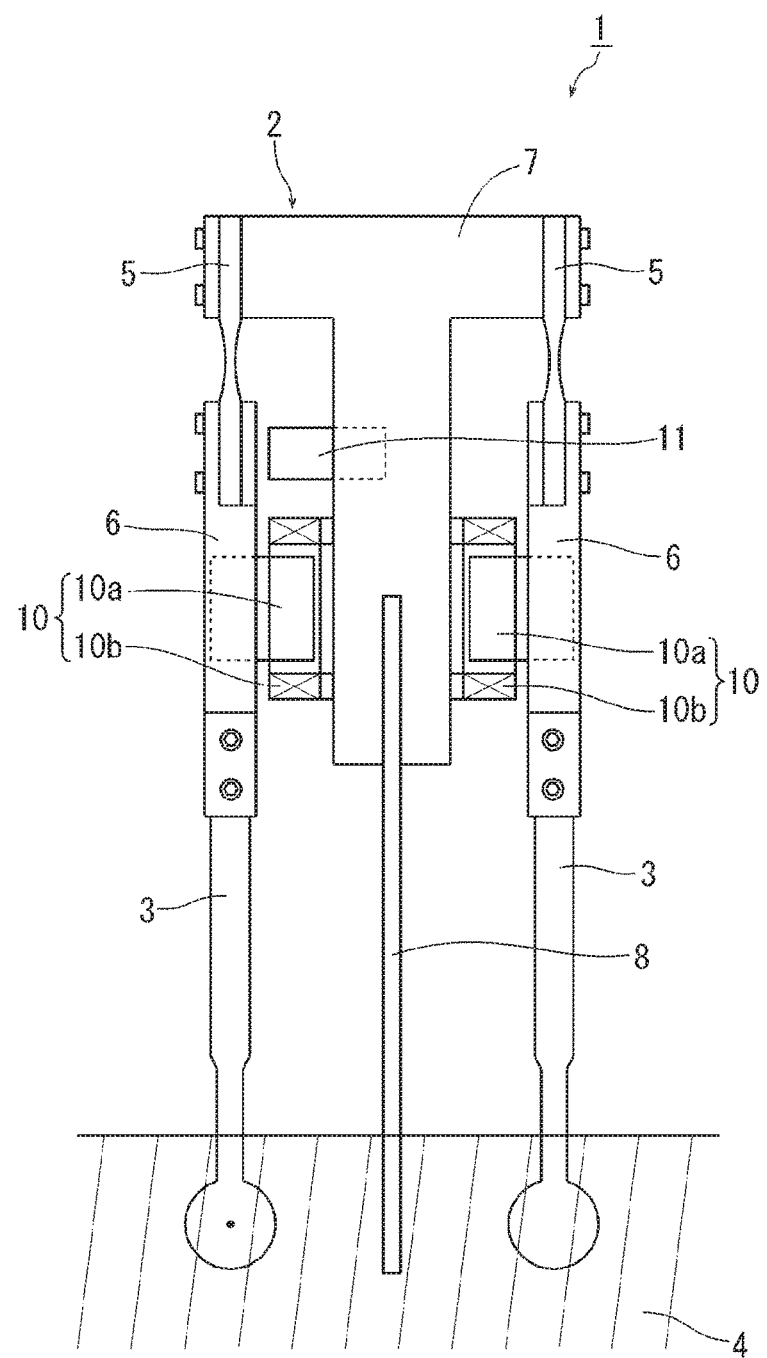
FIG. 1 is a configuration diagram of a drive mechanical part of a tuning fork vibration viscometer.
Figure 2:
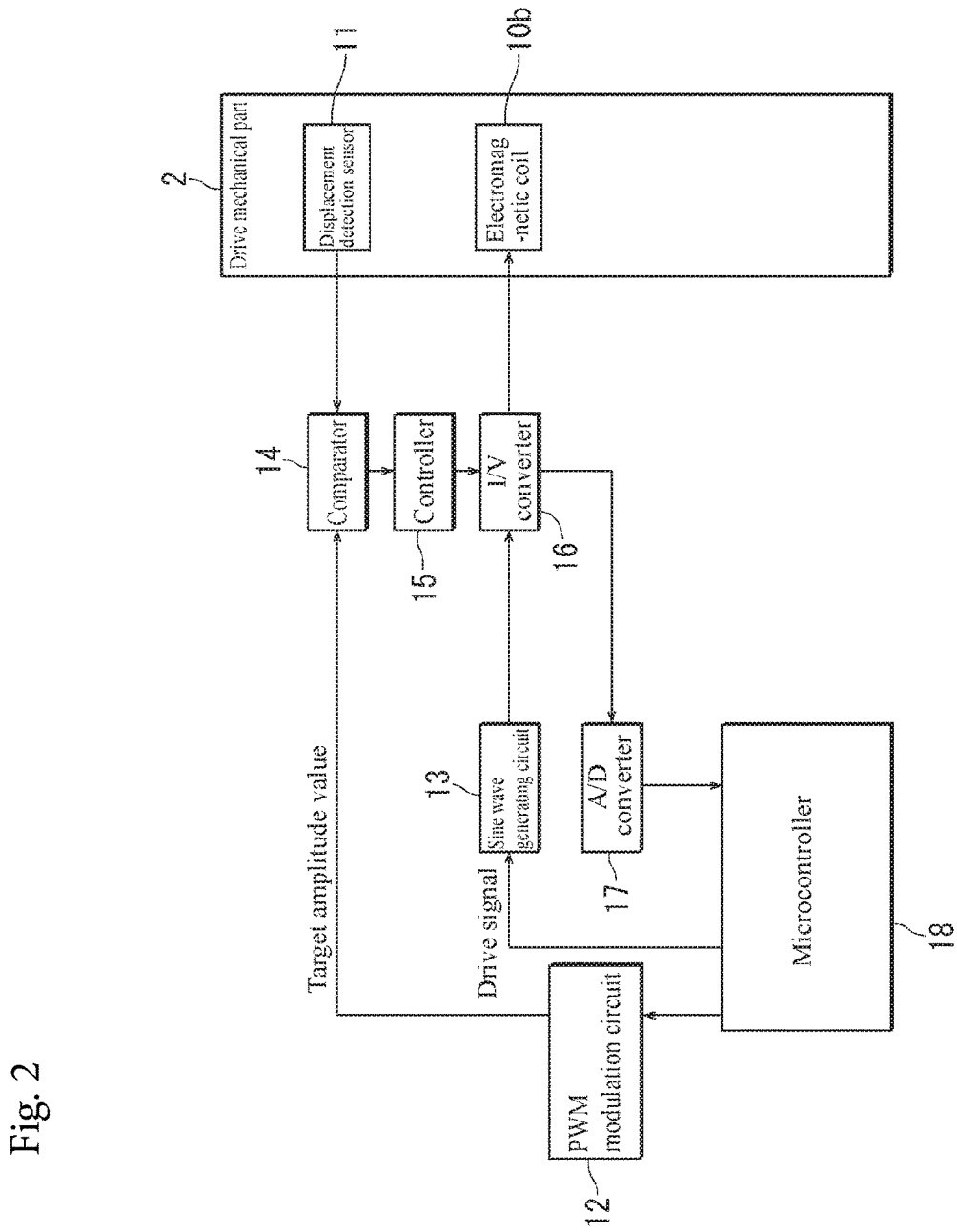
FIG. 2 is a block diagram of a control system of a conventional tuning fork vibration viscometer.
Figure 3:
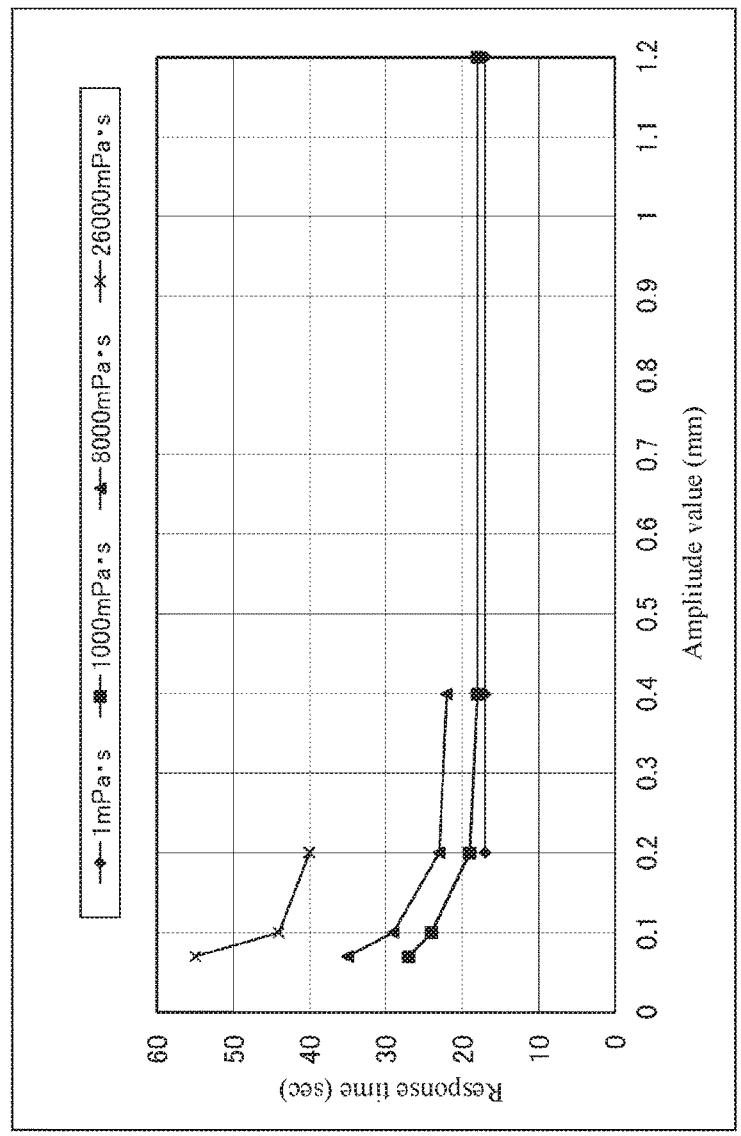
FIG. 3 is a diagram showing a response speed of the conventional tuning fork vibration viscometer.
Figure 4:
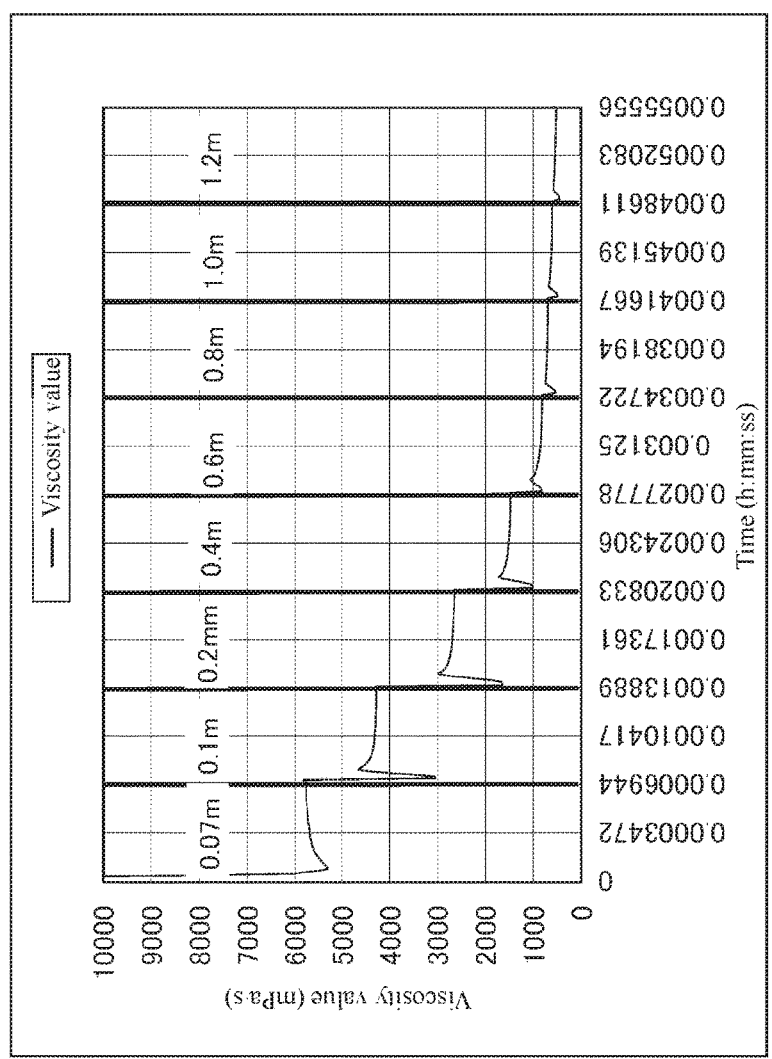
FIG. 4 is a measurement graph obtained with the conventional tuning fork vibration viscometer.
Figure 5:
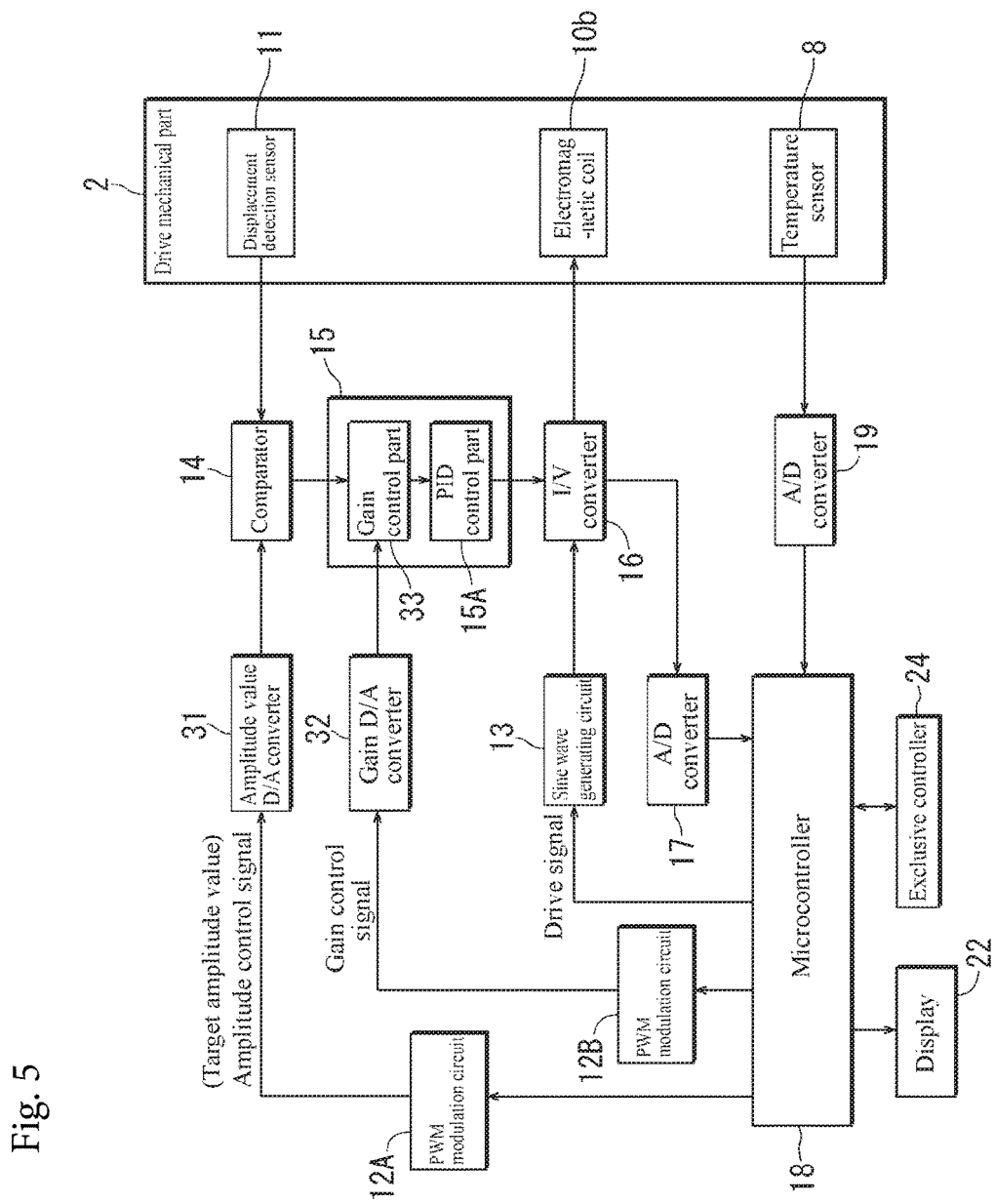
FIG. 5 is a block diagram of a control system of a tuning fork vibration viscometer according to a first embodiment.
Figure 6:
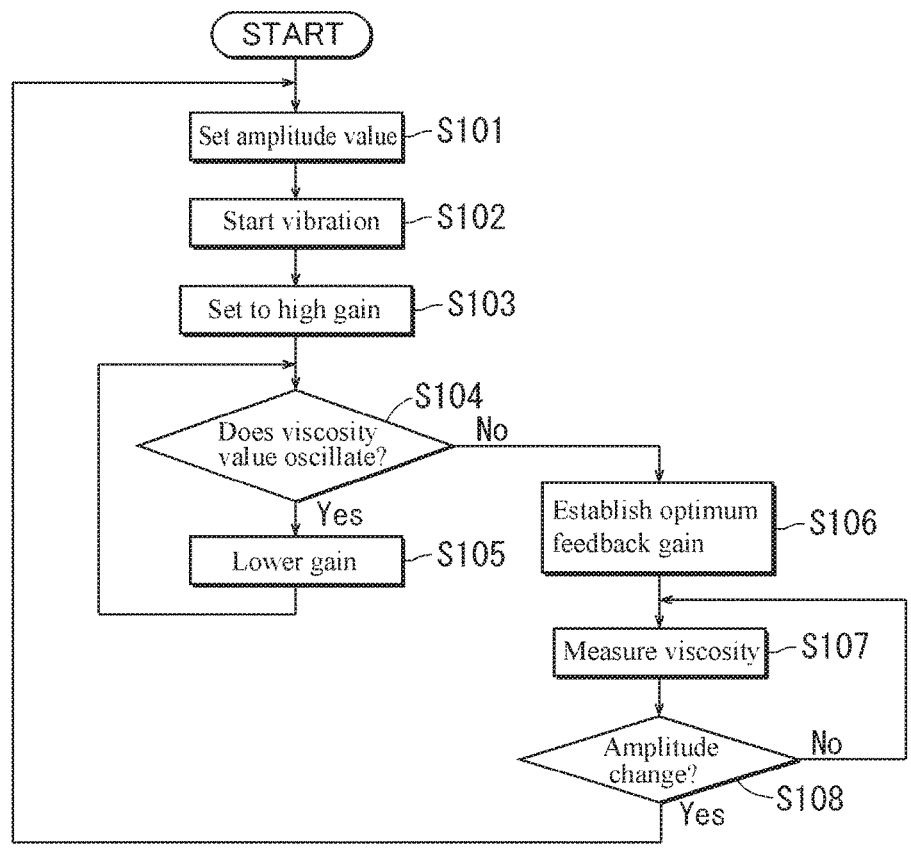
FIG. 6 is a flowchart showing a method of measuring a property of a sample by the tuning fork vibration viscometer according to the first embodiment.
Figure 7:
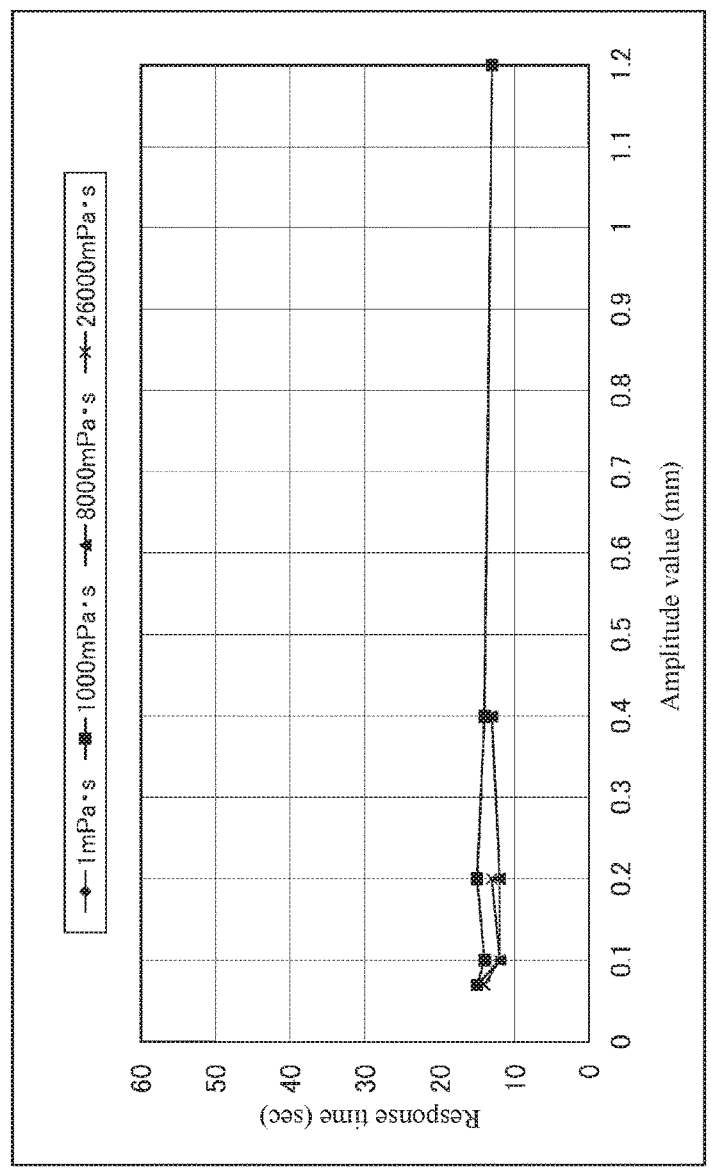
FIG. 7 is a diagram showing a response speed of the tuning fork vibration viscometer according to the first embodiment.
Figure 8:
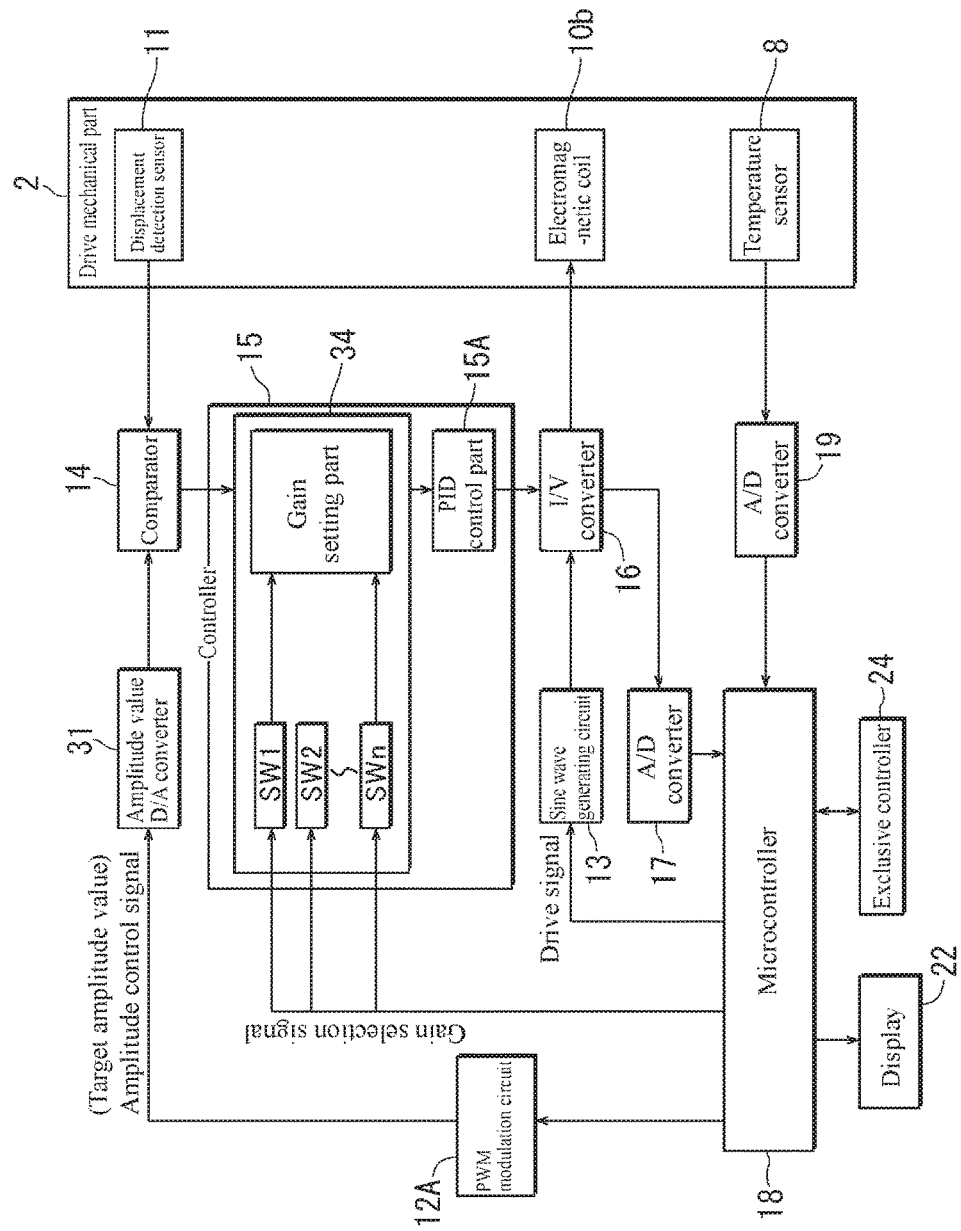
FIG. 8 is a block diagram of a control system of a tuning fork vibration viscometer according to a second embodiment.
Figure 9:
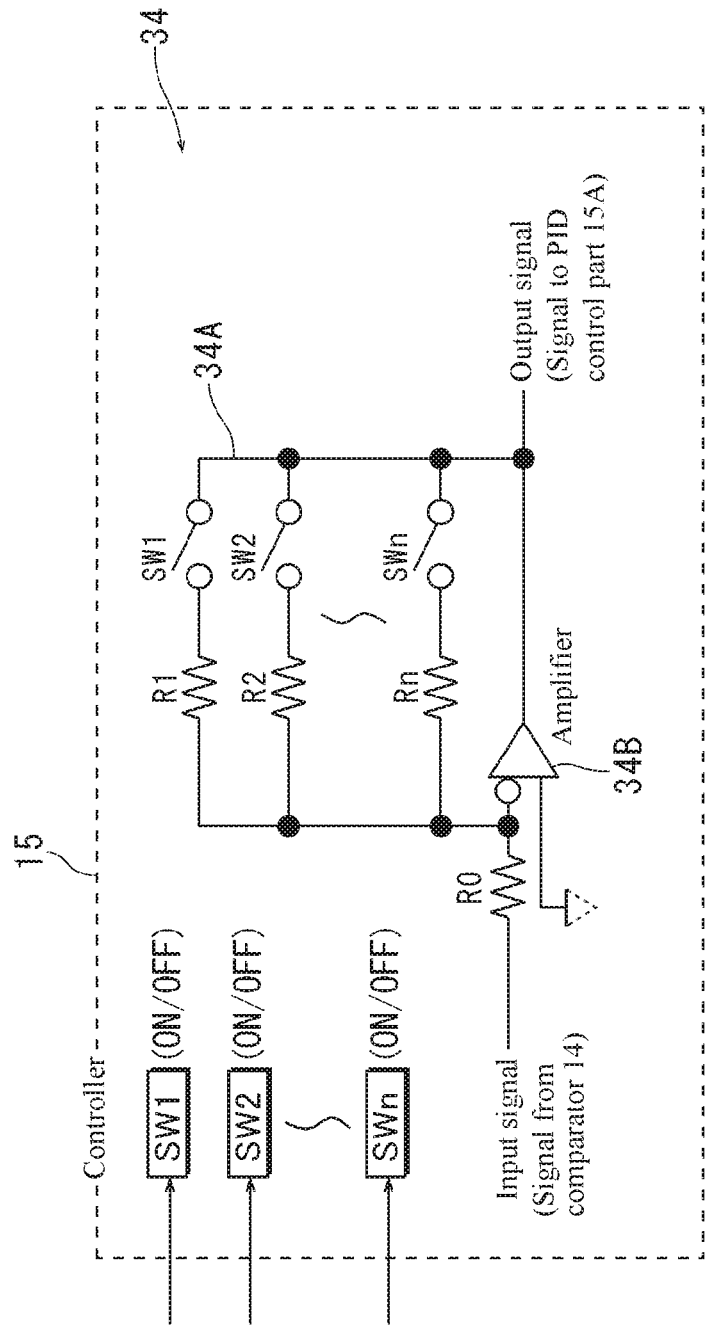
FIG. 9 is a detailed circuit diagram of an essential portion of the same control system.
Figure 10:
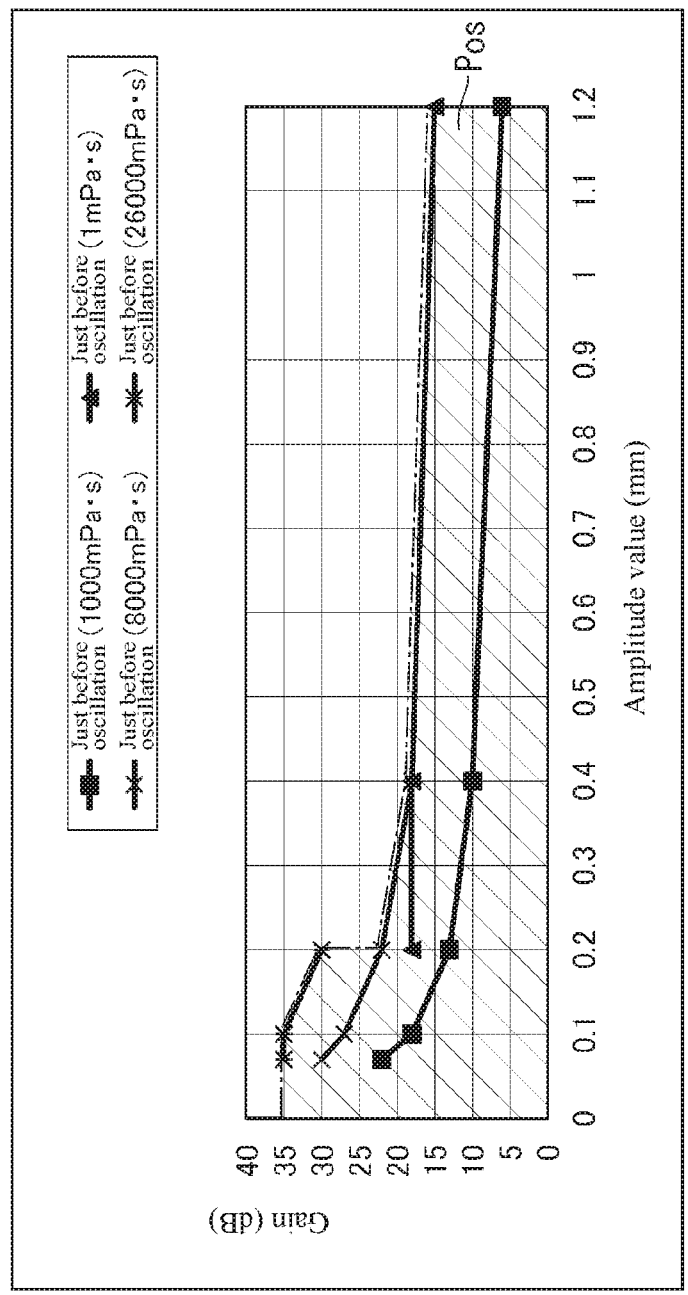
FIG. 10 is a diagram showing an example of an oscillation field.
Figure 11:
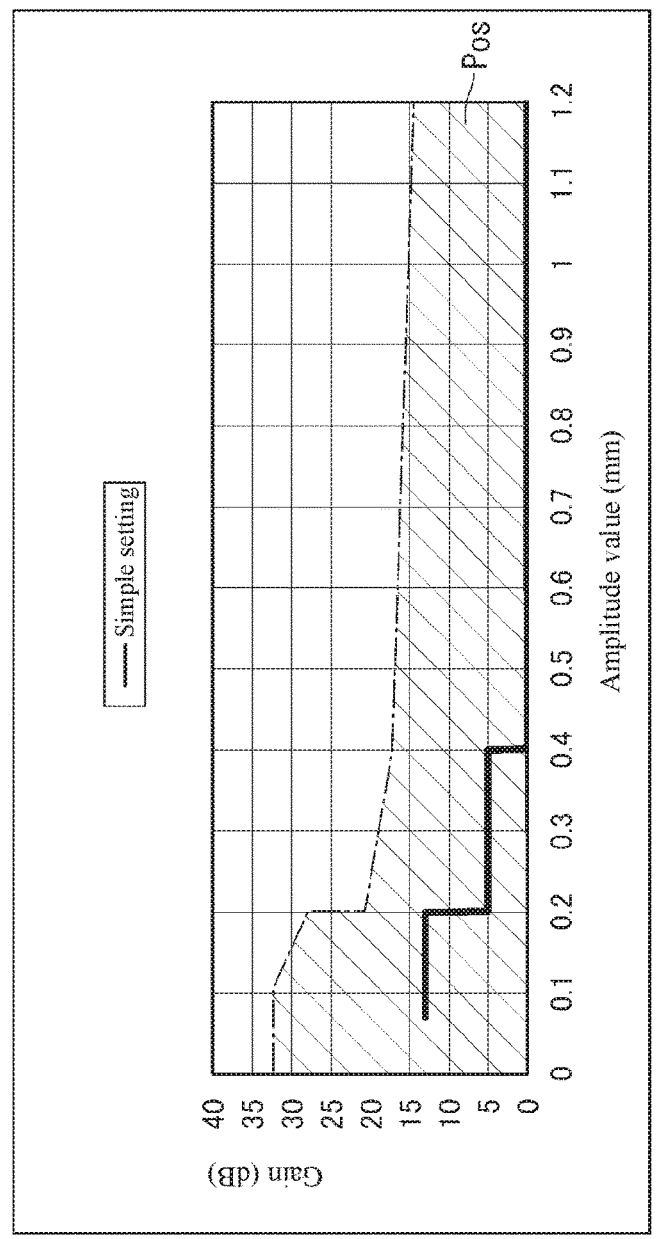
FIG. 11 is a diagram showing an example of simple feedback gain setting.
Figure 12:
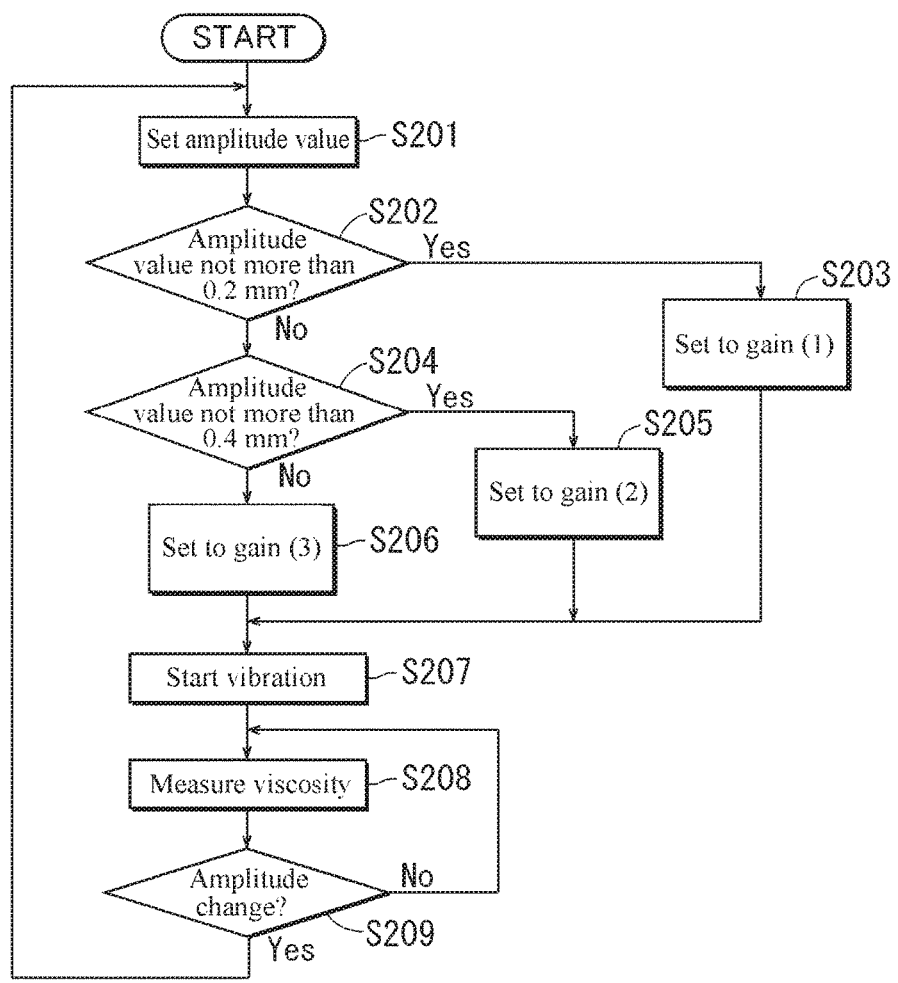
FIG. 12 is a flowchart showing a method of measuring a property of a sample by the tuning fork vibration viscometer according to the second embodiment.
Figure 13:
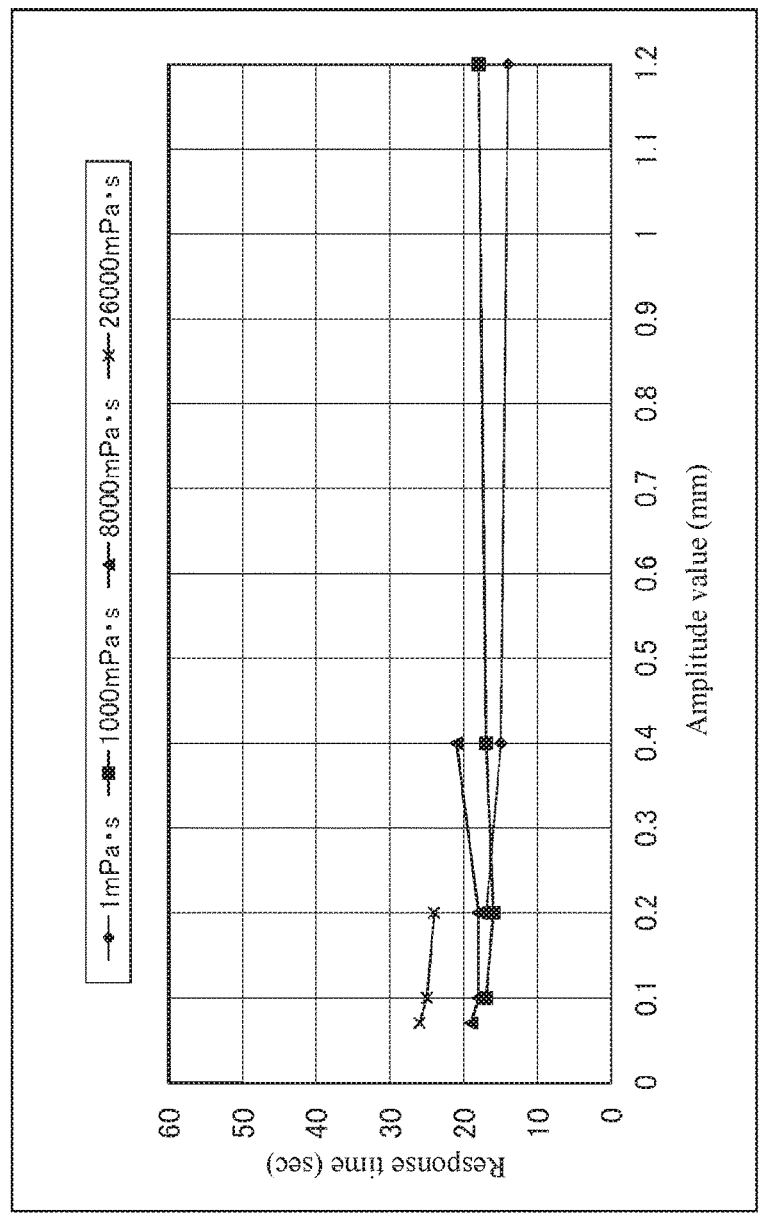
FIG. 13 is a diagram showing a response speed of the tuning fork vibration viscometer according to the second embodiment.
Figure 14:
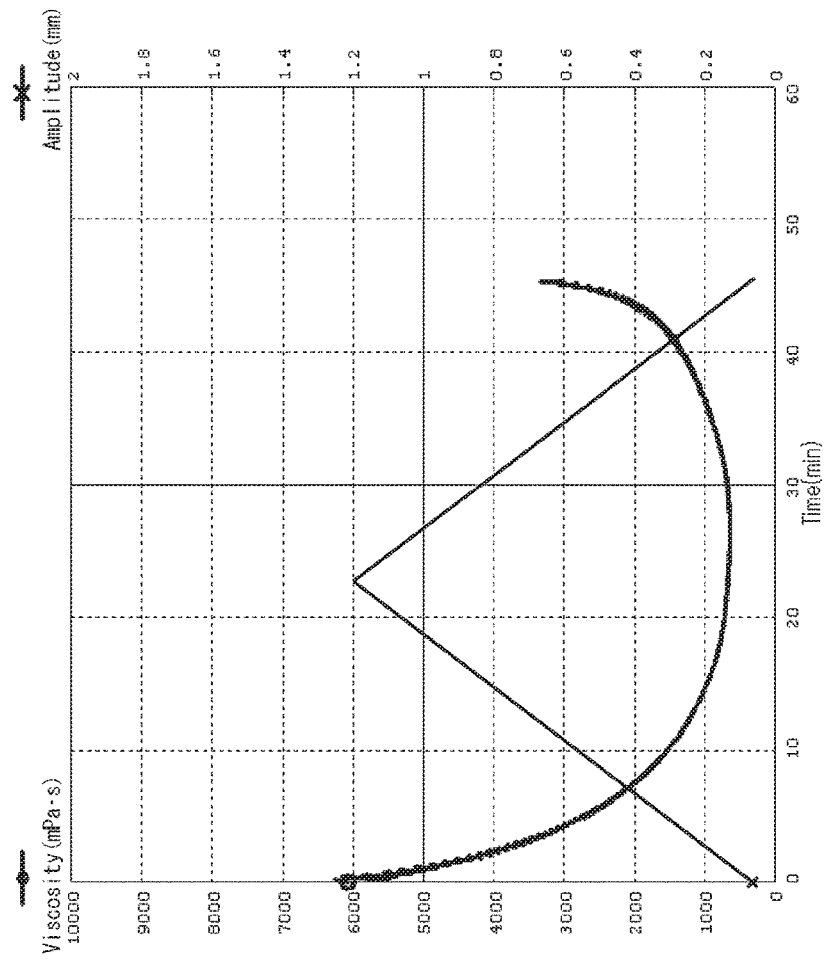
FIG. 14 is a measurement graph obtained with the tuning fork vibration viscometer according to the second embodiment.
Figure 15:
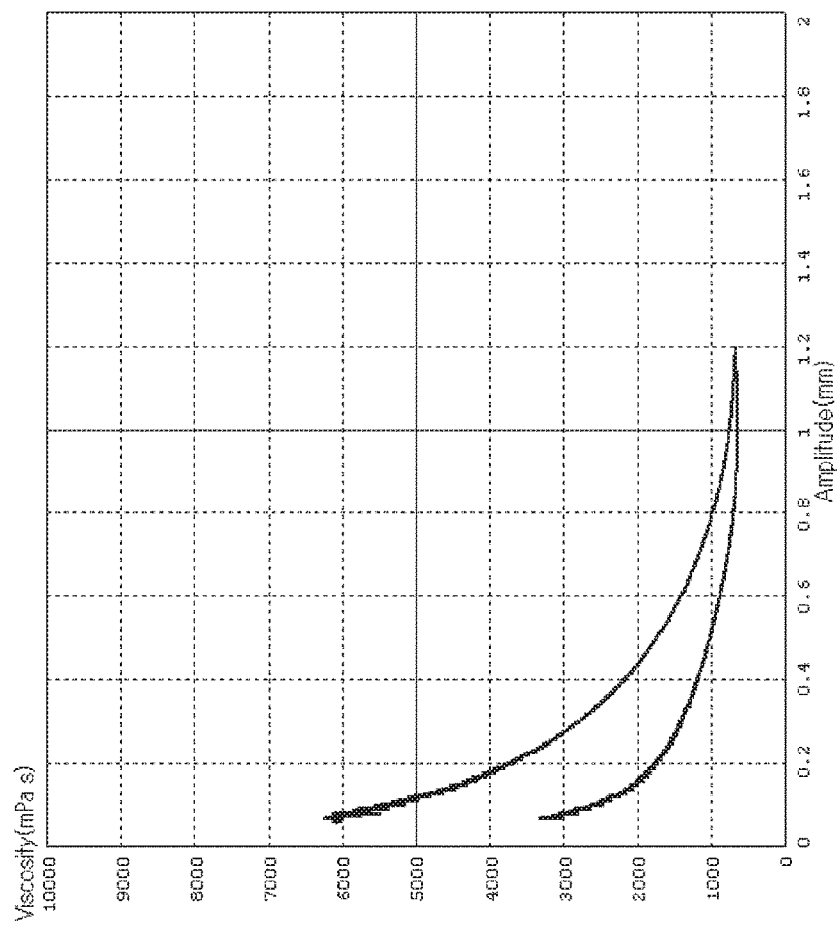
FIG. 15 is a measurement graph obtained with the tuning fork vibration viscometer according to the second embodiment.
Figure 16:
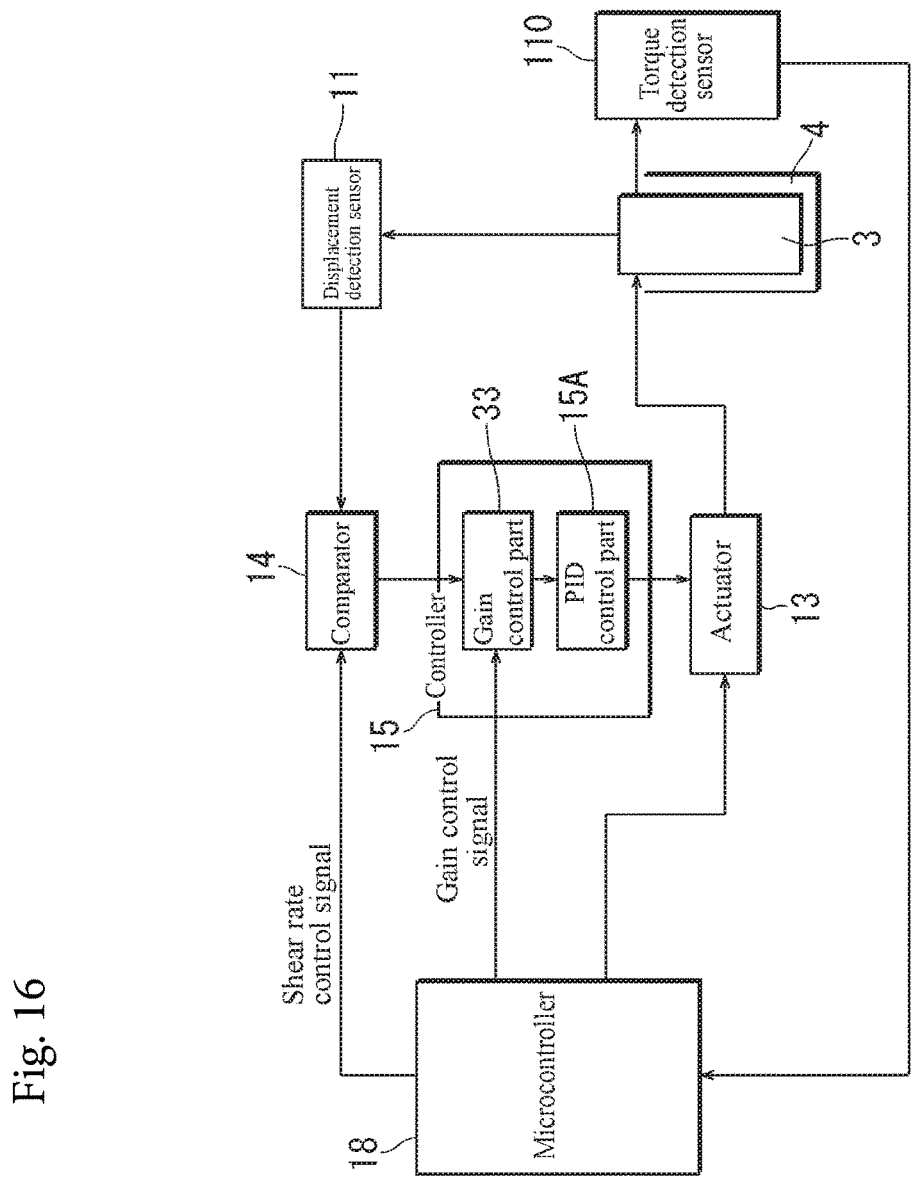
FIG. 16 is a block diagram of a control system of a rotational viscometer according to a third embodiment.
Figure 17:
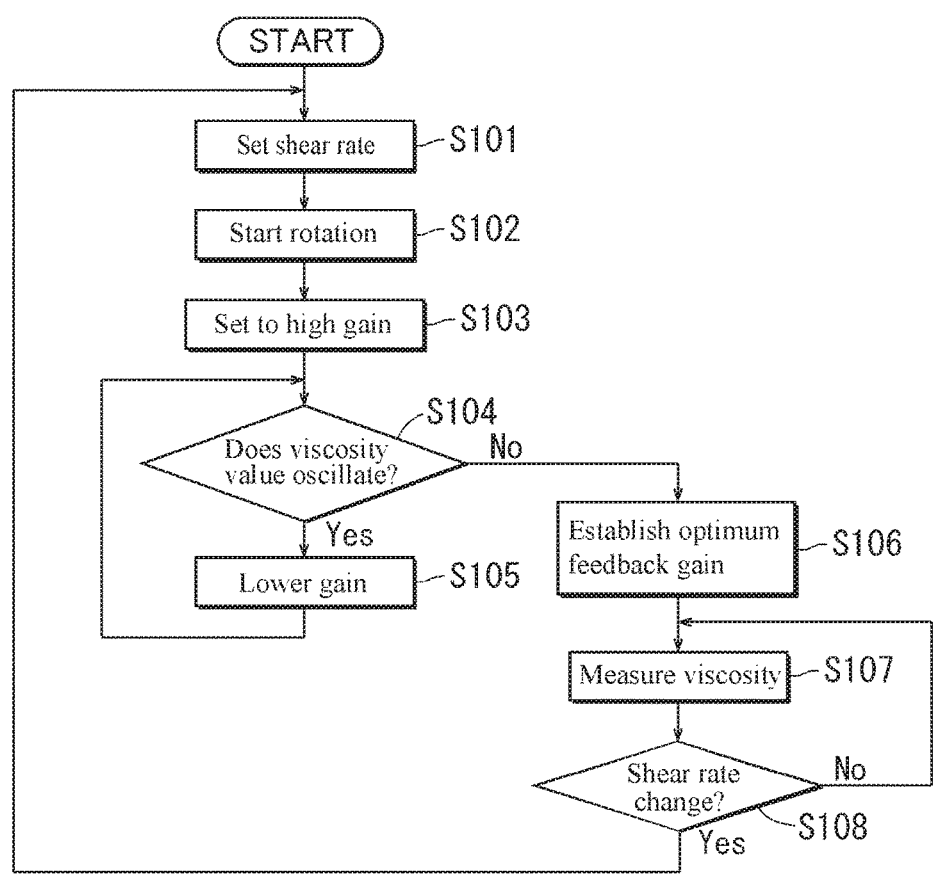
FIG. 17 is a flowchart showing a method of measuring a property of a sample by the rotational viscometer according to the third embodiment.
Figure 18:
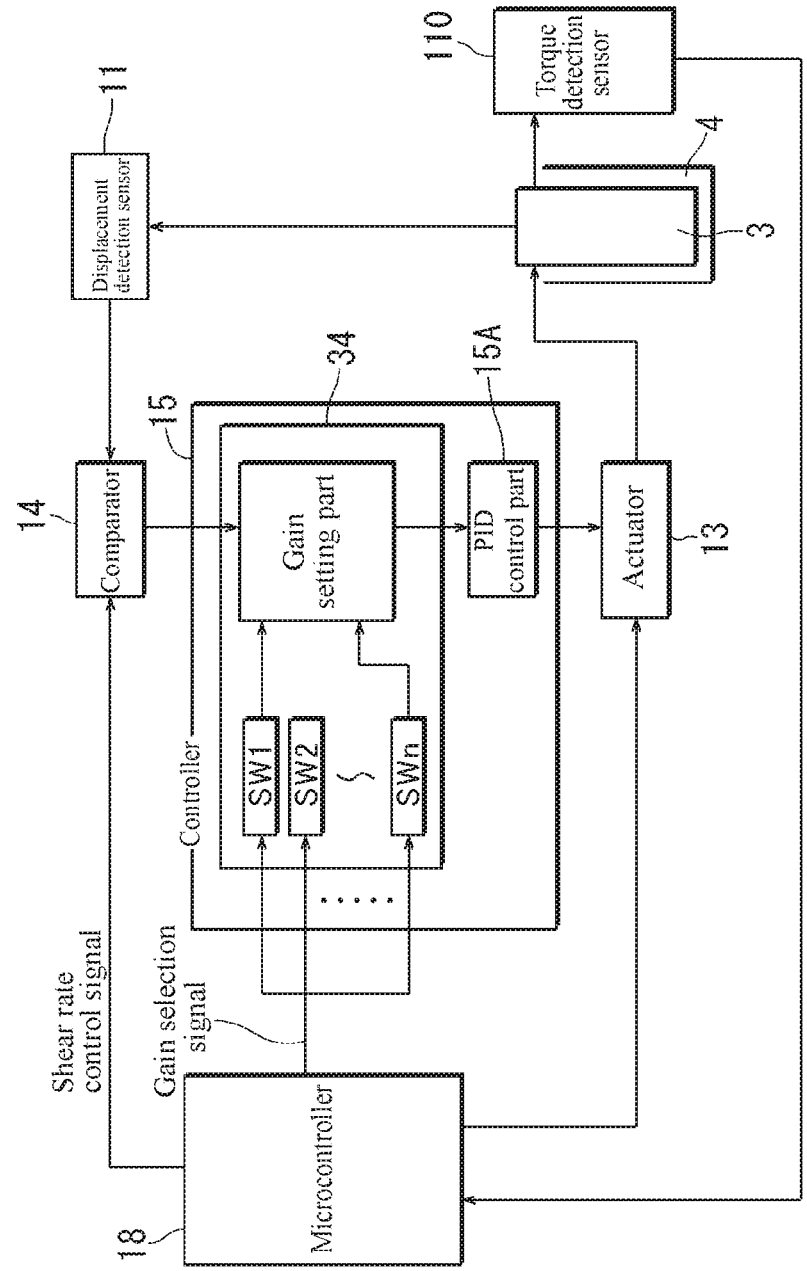
FIG. 18 is a block diagram of a control system of a rotational viscometer according to a fourth embodiment.
Figure 19:
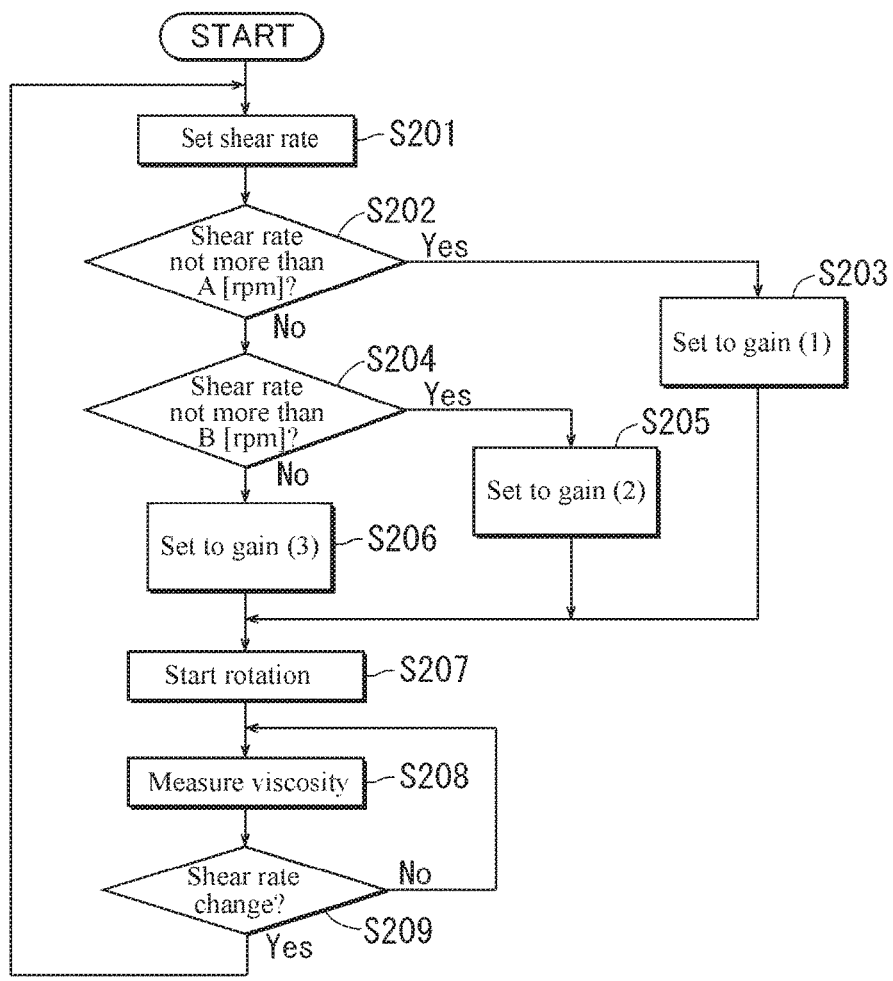
FIG. 19 is a flowchart showing a method of measuring a property of a sample by the rotational viscometer according to the fourth embodiment.

1 Viscometer
3 Vibrator (machine part)
4 Sample
10 Electromagnetic drive
11 Displacement detection sensor
13 Actuator (machine drive)
14 Comparator
15 Controller
18 Microcontroller
33 Gain control part
34 Gain setting part

The invention claimed is:

1. A tuning fork vibration viscometer comprising:
a pair of vibrators to be dunked in a sample;
an electromagnetic drive for vibrating the vibrators;
an amplitude value changing means for outputting a target amplitude value of the vibrators; and
a displacement detection sensor for measuring an amplitude of the vibrators,
and performing feedback control for controlling a driving current applied to the electromagnetic drive so that an output value of the displacement detection sensor corresponds to the target amplitude value and measuring viscosity of the sample based on a value of the driving current, wherein
the tuning fork vibration viscometer further comprises a gain control means that sets a feedback gain in the feedback control high at first, in a state of a specific target amplitude value with respect to a sample having a specific viscosity, reduces the gain until a limiting point that is just before a measured viscosity value starts oscillating is found, defines the gain at the limiting point as an optimum feedback gain, so as to perform a measurement of the viscosity by using the optimum feedback gain, and performs the measurement every time the target amplitude value is changed.

2. A method of measuring a property of a sample by utilizing the tuning fork vibration viscometer according to claim 1, comprising:
setting a feedback gain high at first in the feedback control in a state of a specific target amplitude value with respect to a sample having a specific viscosity;
reducing the gain until a limiting point that is just before a measured viscosity value starts oscillating is found;
defining the gain at the limiting point as an optimum feedback gain, so as to perform a measurement of the viscosity by using the optimum feedback gain, and
performing the measurement every time the target amplitude value is changed.

* * * * *